United States Patent
Su (10) Patent No.: US 8,244,329 B2
(45) Date of Patent: Aug. 14, 2012

(54) MULTIPLE CHANNEL TRACHEAL TUBE PLACEMENT DEVICE AND TECHNIQUE FOR USING THE SAME

(75) Inventor: Mark Su, Boulder, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 353 days.

(21) Appl. No.: 12/569,236

(22) Filed: Sep. 29, 2009

(65) Prior Publication Data

US 2011/0073114 A1  Mar. 31, 2011

(51) Int. Cl.
*A61B 5/00* (2006.01)

(52) U.S. Cl. ............... 600/424; 128/200.26; 128/207.14

(58) Field of Classification Search ................ 600/424; 128/200.26, 207.14, 207.15
See application file for complete search history.

(56) References Cited

U.S. PATENT DOCUMENTS

| | | | |
|---|---|---|---|
| 4,294,263 A * | 10/1981 | Hochman | 600/549 |
| 4,344,436 A | 8/1982 | Kubota | |
| 4,416,289 A | 11/1983 | Bresler | |
| 4,431,005 A | 2/1984 | McCormick | |
| 4,445,501 A | 5/1984 | Bresler | |
| 4,567,882 A | 2/1986 | Heller | |
| 4,943,770 A | 7/1990 | Ashley-Rollman et al. | |
| 5,099,845 A | 3/1992 | Besz et al. | |
| 5,285,778 A | 2/1994 | Mackin | |
| 5,400,771 A | 3/1995 | Pirak et al. | |
| 5,425,370 A | 6/1995 | Vilkomerson | |
| 5,425,382 A | 6/1995 | Golden et al. | |
| 5,437,290 A | 8/1995 | Bolger et al. | |
| 5,445,144 A | 8/1995 | Wodicka et al. | |
| 5,560,351 A | 10/1996 | Gravenstein et al. | |
| 5,622,169 A | 4/1997 | Golden et al. | |
| 5,645,065 A | 7/1997 | Shapiro et al. | |
| 5,785,051 A | 7/1998 | Lipscher et al. | |
| 5,879,297 A | 3/1999 | Haynor et al. | |
| 5,902,238 A | 5/1999 | Golden et al. | |
| 6,129,668 A | 10/2000 | Haynor et al. | |
| 6,132,379 A | 10/2000 | Patacsil et al. | |
| 6,161,537 A | 12/2000 | Gravenstein et al. | |
| 6,164,277 A | 12/2000 | Merideth | |
| 6,216,028 B1 | 4/2001 | Haynor et al. | |

(Continued)

FOREIGN PATENT DOCUMENTS

WO  2009099766  8/2009

OTHER PUBLICATIONS

Roberts, James R. et al., Proper Depth of Placement of Oral Endotracheal Tubes in Adults Prior to Radiographic Confirmation, Academic Emergency Medicine, Jan. 1995, pp. 20-24, vol. 2, No. 1.

(Continued)

*Primary Examiner* — Ruth S Smith
(74) *Attorney, Agent, or Firm* — Fletcher Yoder (57) ABSTRACT

According to various embodiments, a tracheal tube may employ sensing techniques for determining a distance between the inserted tube and an anatomical structure such as a carina. The distance information may provide an indication as to whether or not the tracheal tube is properly placed within the trachea. Because a tracheal tube may rotate within the trachea, the sensing information may be gathered from multiple locations on the tracheal tube for a rotation-independent measurement technique.

24 Claims, 5 Drawing Sheets

U.S. PATENT DOCUMENTS

| | | | |
|---|---|---|---|
| 6,253,770 | B1 | 7/2001 | Acker et al. |
| 6,263,230 | B1 | 7/2001 | Haynor et al. |
| 6,332,089 | B1 | 12/2001 | Acker et al. |
| 6,349,720 | B1 | 2/2002 | Clark |
| 6,453,190 | B1 | 9/2002 | Acker et al. |
| 6,629,924 | B2 | 10/2003 | Aydelotte |
| 6,672,308 | B1 | 1/2004 | Gaspari |
| 6,705,319 | B1 | 3/2004 | Wodicka et al. |
| 6,820,618 | B2 | 11/2004 | Banner et al. |
| 6,849,042 | B2 | 2/2005 | Christopher |
| 6,860,264 | B2 | 3/2005 | Christopher |
| 6,961,600 | B2 | 11/2005 | Kohl et al. |
| 7,052,456 | B2 | 5/2006 | Simon |
| 7,273,050 | B2 | 9/2007 | Wei |
| 2002/0074002 | A1 | 6/2002 | Tung et al. |
| 2004/0221853 | A1 | 11/2004 | Miller |
| 2005/0039754 | A1 | 2/2005 | Simon |
| 2005/0279360 | A1 | 12/2005 | Wei |
| 2006/0036164 | A1 | 2/2006 | Wilson et al. |
| 2006/0081255 | A1 | 4/2006 | Miller et al. |
| 2007/0137652 | A1 | 6/2007 | Qureshi et al. |
| 2007/0299357 | A1 | 12/2007 | Villegas |
| 2008/0039715 | A1 | 2/2008 | Wilson et al. |

OTHER PUBLICATIONS

Pollard, Richard J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Locker, Gottfried J. MD et al., Assessment of the Proper Depth of Endotracheal Tube Placement with the Trachlight, Journal of Clinical Anesthesia, Aug. 1998, pp. 389-393, vol. 10.

Valentino, Joseph MD et al., Utility of Portable Chest Radiographs as a Predictor of Endotracheal Tube Cuff Pressure, Otolaryngology-Head and Neck Surgery, Jan. 1999, pp. 51-56, vol. 1, Issue 120.

Gaspari, Romolo J. MD et al., Magnetically Guided Orotracheal Intubation, Academic Emergency Medicine, Mar. 2001, pp. 285-287, vol. 8, No. 3.

Salem, M. Ramez MD, Verification of Endotracheal Tube Position, Anesthesiology Clinics of North America, Dec. 2001, pp. 1-18, vol. 19, Issue 4.

Juan, Eduardo J. et al., Miniature Acoustic Guidance System for Endotracheal Tubes, IEEE Transactions on Biomedical Engineering, Jun. 2002, pp. 584-596, vol. 49, No. 6.

Kristensen, Michael S. MD, The Parker Flex-Tip Tube Versus a Standard Tube for Fiberoptic Orotracheal Intubation, Anesthesiology, Feb. 2003, pp. 354-358, vol. 98, No. 2.

Kohase, Hikaru DDS, PhD et al., Endotracheal Intubation Device with a Charge Couple Device Camera, Anesthesiology, Dec. 2003, pp. 432-434, Issue 96.

Makino, Hiroshi MD et al., The Effects of Tracheal Tube Tip Design and Tube Thickness on Laryngeal Pass Ability During Oral Tube Exchanger with an Introducer, Anesthesia and Analgesia, Dec. 2003, pp. 285-288, Issue 97.

Chun, Rosaleen, MDm FRCPC et al., Where's the Tube? Evaluation of Hand-held Ultrasound in Confirming Endotracheal Tube Placement, Prehospital and Disaster Medicine, Nov. 2004, pp. 366-369, vol. 19, No. 4.

Monitoring of Intubation and Ventilation During Resuscitation, http://clinicaltrials.gov/ct2/show/NCT00204217, ClinicalTrials.gov, Sep. 2005, pp. 1-3.

O'Connor, Christopher J. MD et al., Identification of Endotracheal Tube Malpositions Using Computerized Analysis of Breath Sounds via Electronic Stethoscopes, Anesthesia and Analgesia, Dec. 2005, pp. 735-739, Issue 101.

Sehata, H et al., Tracheal Intubation using a new CCD Camera-Equipped Device: A Report of Two Cases with a Difficult Intubation, Acta Anaesthesiologica Scandinavica, Dec. 2005, pp. 1218-1220, Issue 49.

Weaver, Blake et al., Confirmation of Endotracheal Tube Placement after Intubation Using the Ultrasound Sliding Lung Sign, Academic Emergency Medicine, Mar. 2006, pp. 239-244, Issue 13.

Kaplan, M. B. et al., Seeing is Believing: the Importance of Video Laryngoscopy in Teaching and in Managing the Difficult Airway, Surgical Endoscopy and Other Interventional Techniques, Mar. 2006, pp. S479-S483, Issue 20.

Fridman, Ofer, Visual Sensor Provides a Breath of Fresh Air for Medical Ventilation, Medical Design Technology, Jul. 2006, pp. 11-13.

Schwarz, Uwe MD, Validation of Supra-Sternal Tube-Tip Palpatation (SSTTP), http://clinicaltrials.gov/ct2/show/NCT00690508, ClinicalTrials.gov, Aug. 2010, pp. 1-4.

Karsli, Cengiz, Head Movement Effect on Different Tracheal Tubes, http://clinicaltrials.gov/ct2/show/NCT00687583,ClinicalTrials.gov, Aug. 2010, pp. 1-3.

Wichakook, Warit et al., Magnetic Endotracheal Tube Imaging Device, 30th Annual International IEEE EMBS Conference, Vancouver, Canada, Aug. 20-24, 2008, pp. 985-988.

Cohen Endobronchial Blocker, Cook Medical, http://www.cookmedical.com/cc/dataSheet.do?id=3989, Mar. 2010, pp. 1-2.

Rusch, Easytube Double Lumen, Teleflex Medical, http://www.teleflexmedical.com/prod_rusch.php, 2009, pp. 1-7.

Portex, Endobronchial Double Lumen, Anesthesia Airway, http://www.smiths-medical.com/catalog/endobronchial-tubes/blue-line-endobronchial-tubes1.html, Apr. 2010, pp. 1-13.

Arndt Endobronchial Blocker, Cook Medical, http://www.cookmedical.com/cc/dataSheet.do?id=3988, Mar. 2010, pp. 1-4.

* cited by examiner

MULTIPLE CHANNEL TRACHEAL TUBE PLACEMENT DEVICE AND TECHNIQUE FOR USING THE SAME

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated when an endotracheal tube is inserted through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube's position within the trachea that may occur when a patient coughs, which may dislodge a tube from its desired location, or when a patient is jostled or moved within a care setting, which may change the position or angle of the tube within the trachea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient's trachea at a location substantially between the patient's vocal cords and carina. If the tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Provided herein are tracheal tubes and systems for facilitating proper placement of the tracheal tube relative to certain anatomical structures in and around the patient's airway and trachea. Such tracheal tubes may include assemblies for emitting energy (e.g., electromagnetic energy, ultrasound waves, acoustic waves) and detecting the returned energy. For example, when light is emitted from a device, the returned light may be detected after being reflected/scattered by internal tissues of the patient (such as the tissues in the vicinity of the carina). Accordingly, information related to the detected light, for example its phase relative to a reference, its time of flight, and/or its intensity may be used to determine a distance from the tube to the anatomical structure in question. In addition to being applied to optical or electromagnetic energy, such determinations of phase, time of flight, and/or intensity may be applied to other types of emissions, such as ultrasound or acoustic emissions, to determine information about the placement of the endotracheal tube. For example, such information may be used to determine a distance from the distal end of the tracheal tube to the carina (or other internal anatomical structure or tissue). A healthcare provider may then use the information about the location of the tracheal tube relative to the anatomical structures (e.g., the carina) to determine whether the tube is properly placed or whether the position of the tube should be adjusted.

As provided herein, tracheal tubes and systems may include multiple energy emitters and detectors for capturing information associated with multiple locations on or around the tube. Tracheal tubes are intended to be inserted into the patient in a certain rotational orientation. However, a particular tracheal tube may be inserted in a different orientation or may become twisted or rotated during the course of the intubation. As a result of rotational variability of each individual tube in the patient, the pathway of any energy emitted from a particular location on the tube may be highly dependent on the orientation of the tube. For example, a change in the rotation of a tube may cause energy to be emitted towards the lungs rather than into a tracheal wall. As a result, the energy may have a correspondingly longer pathway before encountering solid tissue, which may in turn result in lower intensity of the returned energy or a longer time of flight. Accordingly, in embodiments in which a single energy emitter is employed, such potential pathlength variability may result in a range of potential measurements with regard to the location of the distal tip of the tube. By using multiple measurement locations on the tracheal tube, for example measurement locations distributed about the rotational axis of the tube, the effects of rotational variability may be avoided, compensated for, or cancelled so that the determination of the distal tip placement relative to anatomic structures may be relatively independent of tube rotation.

In embodiments described herein, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
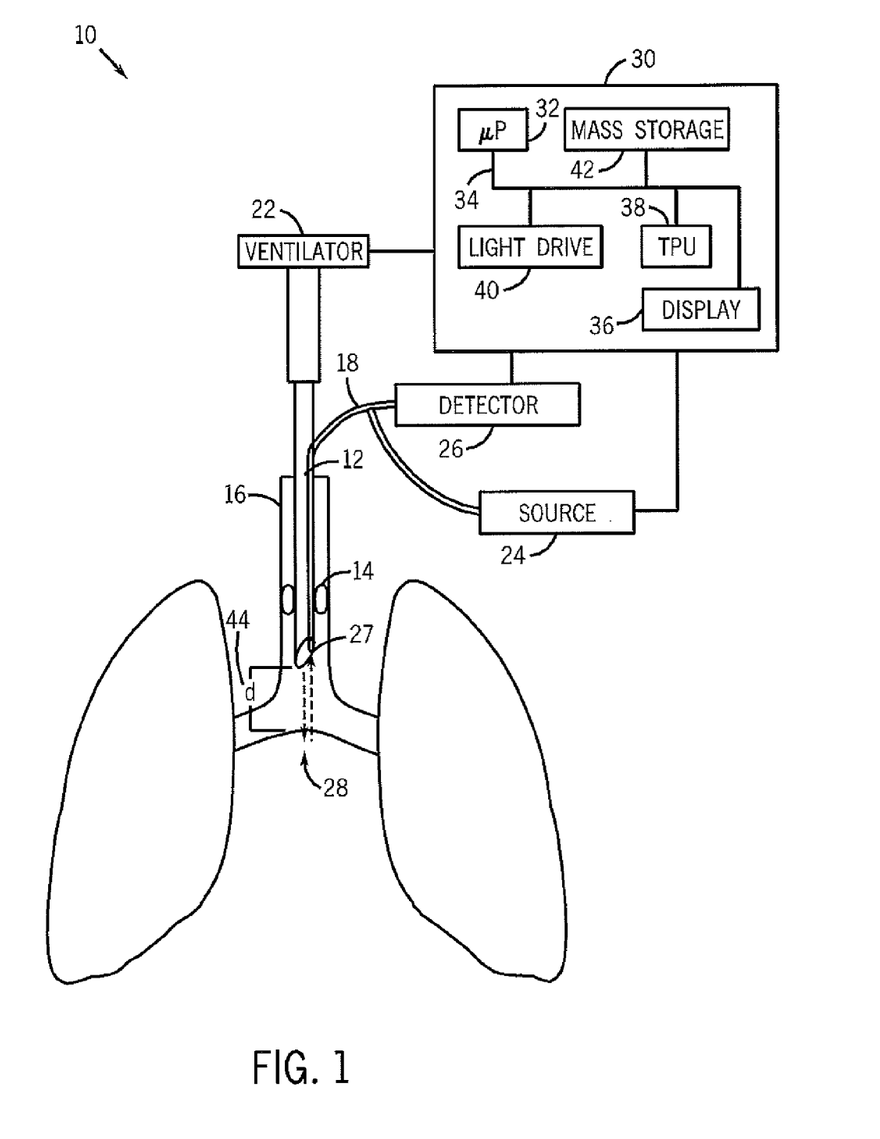
FIG. 1 illustrates an exemplary system including an tracheal tube with an energy source and detector.

FIG. 1 shows an exemplary tracheal tube system 10 that has been inserted into a patient's trachea. The system 10 includes a tracheal tube 12, shown here as endotracheal tube, with an inflatable balloon cuff 14 that may be inflated to form a seal against tracheal walls 16. When ventilation is provided via the tube system, a ventilator 22 is typically provided, as discussed below. As shown, the tracheal tube 12 may also include energy conducting channels 18 to direct the energy from one or more proximally located sources 24 through the tube 12 to be emitted from a plurality of predetermined locations on the tube 12. In certain embodiments, separate return conducting channels 20 may be provided that are associated with the tube 12 to transmit the returned energy to one or more detectors 26. However, in other embodiments, the emitted energy may return through the same conducting channel 18 through which the energy is emitted. For example, the energy conductors may include optical fibers configured to pass light from one or more light sources through a distal end 27 of the endotracheal tube and into a patient's trachea such that a portion of the emitted light may interact with the carina 28 of the patient. The emitted light may be transferred back through an optical detection fiber, which may be coupled to one or more light detectors. Further, in alternate embodiments, the tube 12 may employ energy sources 24 and detectors 26 mounted directly on the tube 12, which may eliminate the need for conducting channels 18 and 20 to transmit energy to and from proximally located components.

When the system 10 includes devices that facilitate positive pressure ventilation of a patient, such as ventilator 22, any ventilator may be used, such as those available from Nellcor Puritan Bennett LLC. The system may also include a monitor 30 that may be configured to implement embodiments of the present disclosure. The monitor 30 may be a stand-alone device or may be coupled to another patient monitor or to the ventilator 22. The monitor 30 may include a microprocessor 32 coupled to an internal bus 34 and a display 36. Regardless of where it is placed, the microprocessor, or any other suitable processing circuitry, aids in computing the distance of the distal end 27 of the tube from reference structures within the patient, such as the carina 28.

The monitor 30 may include certain elements for controlling the energy source 24 and the detector 26. The monitor 30 may drive energy from an individual source 24, which in turn may be carried by one or more energy conducting channels 18. The energy may pass into or impact the tissue, where it may be variously scattered, absorbed, and/or reflected and then detected by detector 26. A time processing unit (TPU) 38 may provide timing control signals to drive circuitry 40, which controls when the energy source 24 is activated, and if multiple sources 24 are used, the multiplexed timing for the different sources. TPU 38 may also control the gating-in of signals from detector 26.

The monitor 30 may be configured to receive signals from the detector 26 and store the signals, or values derived from the signals in a mass storage device 42, such as a RAM, ROM, optical storage device, flash memory device, hardware storage device, a magnetic storage device, or any other suitable device permitting memory storage. The signals or values may be accessed and operated on according to instructions (which may also be stored in the memory circuitry) executed by the microprocessor 32. In certain embodiments, the signals or values may be related to a placement of the tracheal tube 12 within the patient's trachea and may be processed by the monitor 30 to indicate whether the tracheal tube 12 is properly placed. The monitor 30 may be configured to provide an indication about the placement of the tracheal tube 12 within the patient's trachea, such as an audio alarm, visual alarm or a display message if the tracheal tube 12 is too far or too close to certain anatomical structures, such as the carina 28, or outside of a predetermined placement range. In an exemplary embodiment, based at least in part upon the received signals corresponding to the light received through return conducting channels 20, microprocessor 32 may calculate a placement parameter of the endotracheal tube 12 using various algorithms. The placement parameter may relate to, measure, or provide an indication of a distance 44 between the distal end 27 of the tube 12 and the carina 28 or other anatomical structure.

The energy source 24 and detector 26 may be of any suitable type. For example, the source 24 may be one or more light emitting diodes adapted to transmit one or more wavelengths of light, for example in the red to infrared range, and the detector 26 may be one or more photodetectors selected to receive light in the range or ranges emitted from the light source 24. A light source 24 may be a coherent light source, such as a laser diode or a vertical cavity surface emitting laser (VCSEL). The light source 24 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. It should be understood that, as used herein, the term "energy" may refer to one or more of various forms of electric, magnetic or electromagnetic energy, such as in any one or more portions of the spectrum, including radio, microwave, millimeter wave, infrared, visible, ultraviolet, gamma ray or X-ray. Further, as provided herein, "energy" may include acoustic energy, such as ultrasonic energy. In the latter case, for example, source 24 and detector 26 may be part of a transceiver structure configured to transmit ultrasound or acoustic waves through energy conductors 18 and/or return conducting channels 20. In such embodiments, the source 24 and detector 26 may be part of a single structure.

Figure 2:
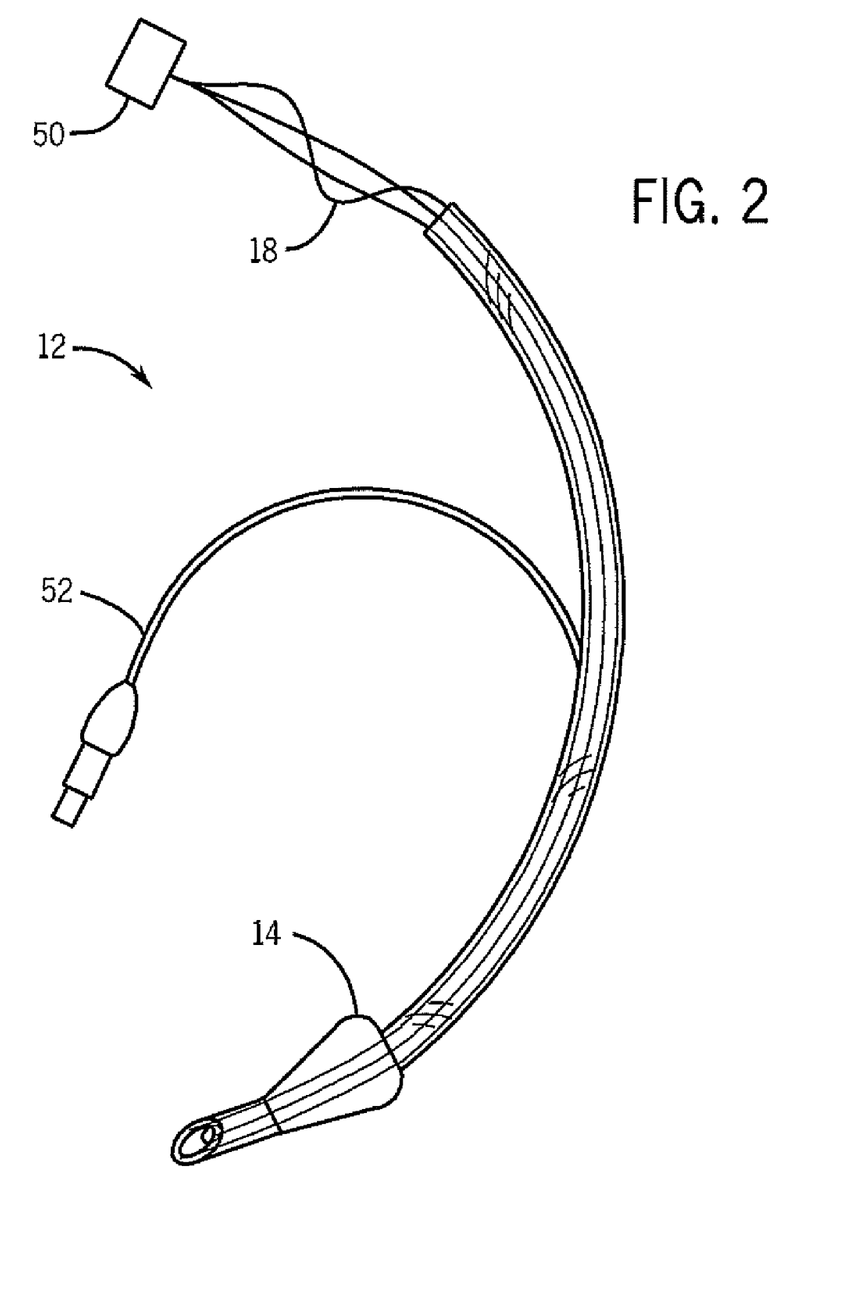
FIG. 2 is a perspective view of an exemplary tracheal tube.

FIG. 2 is a perspective view of an exemplary tracheal tube 12 according to certain embodiments that includes an electrical connector 50 for connecting the electrical and/or optical conducting components (e.g., conducting channels 18 and/or 20) to an upstream monitor 30. The connector 50 may include a memory or other machine-readable hardware or software components to allow identification and calibration of the energy conductors. Further, the electrical connector 50 may provide an interface for connecting energy conducting channels 18 and, optionally, conducting channel 20, to any associated energy sources 24 and detectors 26.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In one embodiment, the cuff 14 may be generally sized and shaped as a high volume, low pressure cuff that may be designed to be inflated to pressures between about 15 cm $H_2O$ and 30 cm $H_2O$. The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene. As shown, the tube 12 may include a cuff 14 that may be inflated via inflation lumen 52.

Figure 3:
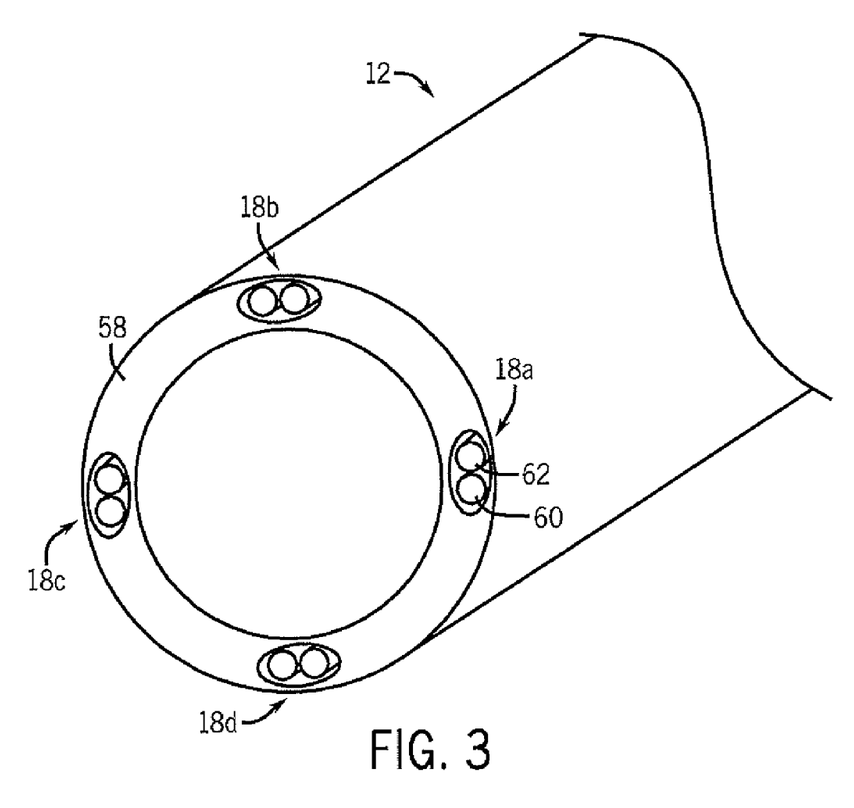
FIG. 3 is a cross-sectional view of a tracheal tube with multiple channels that include embedded optical fibers.

The tracheal tube 12 may also include a plurality of electrical conducting channels 18, which may be disposed on or around the tube in any suitable arrangement. For example, as shown in FIG. 3, which is cross-sectional view of the tube 12, the conductors 18 and 20 may include optical fibers that are embedded in a wall 58 of the tube 12 to form a single energy conducting channel 18. For example, conducting fiber 60 and return fiber 62 may form energy conducting channel 18a. Similar channels 18b, 18c, and 18d including fibers or fiber bundles may be distributed about the tube wall 58. In certain embodiments, fibers 60 and 62 may include individual fibers or fiber bundles with multiple conducting and return fibers. In certain embodiments, the transmitting and detecting may also take place within a single fiber. The energy conductors 18 may extend through the walls 58 of the tracheal tube 12 such that they are substantially in line with a flow path of the tracheal tube 12. Further, the path of the fibers (e.g., 60 and 62) through the wall 58 of the tube 12 may be manipulated to avoid or be diverted around certain openings in the tube 12, such as the Murphy eye or any inflation lumen openings. As energy loss to optical fibers may be minimal, such diversion around may not have any substantial impact on the emitted or returned energy intensity, although the length of any fibers may be related to time of flight measurements, which may be accounted for by appropriate calibration.

Figure 4:
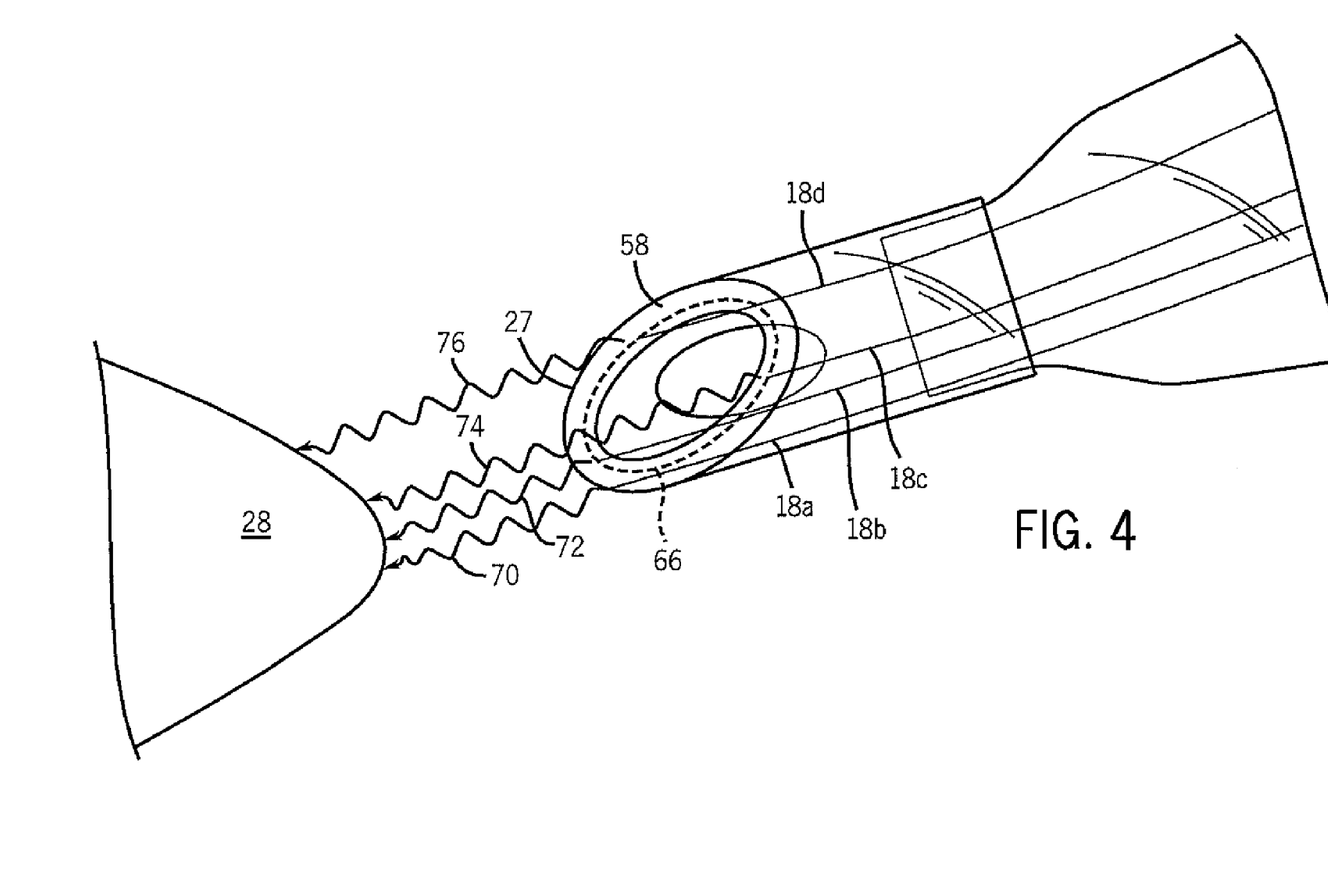
FIG. 4 is a perspective view of an exemplary distal tip of a tracheal tube with embedded optical fibers.

FIG. 4 is a side view of the distal end 27 of the tracheal tube 12. At the distal end 27, the energy conducting channels 18 embedded or formed in the walls 58 of the tracheal tube may terminate such that the energy is emitted through the distal end 27, which may be cut on a slant to facilitate insertion of the tube 12 in the trachea. The terminated ends of the energy conducting channels 18 may be distributed around the circumference 66 of the tube wall 58. In an exemplary embodiment, four channels 18 may be substantially evenly spaced about the circumference 66. In other embodiments, two channels 18, three channels 18, or more than four channels 18 may be used. As shown, the positioning of the channels 18 around the circumference 66 may influence the path of the light from the distal end 27 of the tube 12 to the anatomical structure. Arrows 70, 72, 74, and 76 illustrate four different light paths from bundles 18a, 18b, 18c, and 88d, respectively, to anatomical structures at or proximate to the carina 28. Arrow 70 has a somewhat shorter path than arrow 76, which is related to its position around the circumference 66 relative to the carina 28, as well as differences in the topography of the carina 28. In addition, slight changes in the angle within the trachea of the distal end 27 of the tube 12 may influence the path of light to and from the channels 18.

Figure 5:
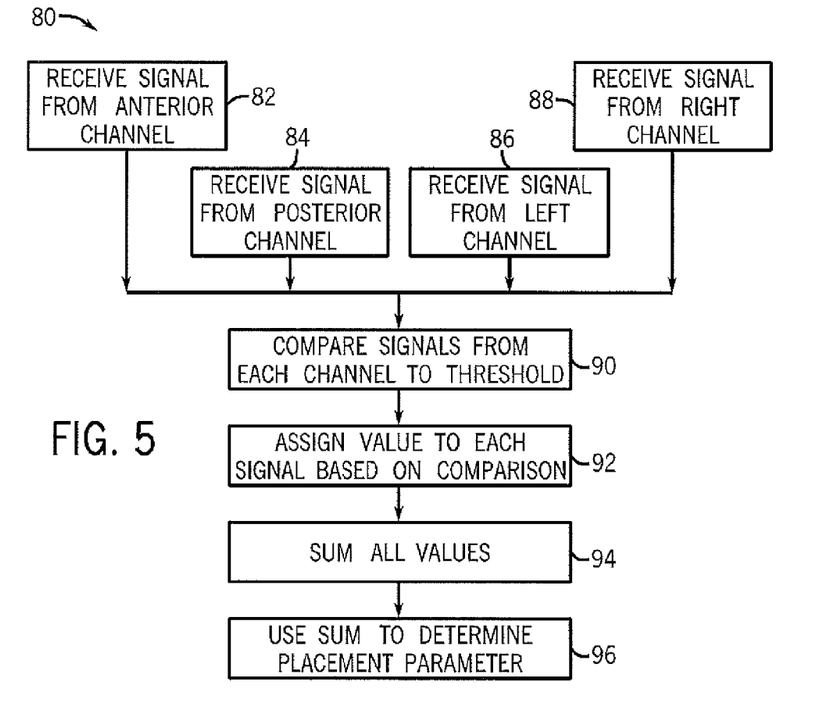
FIG. 5 is a flow diagram of an exemplary method of determining tracheal tube placement.

FIG. 5 is a process flow diagram illustrating a method in accordance with some embodiments. The method is generally indicated by reference number 80 and includes various steps or actions represented by blocks. It should be noted that the method 80 may be performed as an automated procedure by a system, such as system 10. Further, certain steps or portions of the method may be performed by separate devices. In embodiments, the method 80 may be performed continuously or intermittently for long-term patient monitoring or at any appropriate interval depending on the particular situation of the intubated patient. Further, the steps of method 80 may be performed during insertion of the tracheal tube 12 into the patient.

According to an exemplary embodiment, the method 80 begins with receiving a signal from one or more detectors related to energy from source 24 detected by detector 26. Any energy that is returned through the energy conducting channel 20 and received by the detector 26 may carry information about the relative position of the tube 12 and the anatomical structure that is carried in the sample signal. For embodiments in which there are four energy conducting channels 18 evenly distributed about a distal end 27 of the tube 12, the channels 18 may be referred to by their locations. For example, the channels 18 may include anterior, posterior, left, and right channels 18, whose signal may be received either substantially simultaneously or in series at blocks 82, 84, 86, and 88, respectively.

At block 90, a monitor 30 may perform analysis of the each signal in turn by comparing the signal, either raw or processed, to a threshold. For example, the threshold may be an empirically-determined threshold that is associated with proper placement of the distal end 27 with regard to the carina 28. For example, proper tube placement may involve an estimated distal end 27-carina 28 separation distance 44 of 1-5 cm. It should be appreciated that there may be several empirically derived target distances, depending on the size, age, or gender of the patient. A target distance to which the measured distance 44 may be compared may differ for adult men, who may have, in an embodiment, a predetermined target of 3-4 cm, and adult women, for whom the predetermined target may be 2-3 cm. In other embodiments, an alarm or other indication may be triggered if the distance 44 is determined to be less than 3 cm, less than 2 cm, or less than 1 cm.

The threshold may be determined by measuring the distance from the distal end 27 to the carina 28 in an inserted tube 12 by imaging techniques while emitting and detecting energy. Such analysis may also be done with an artificial trachea system. The intensity and/or time of flight measurements associated with proper placement may be used to determine a threshold measurement which may be used to perform the comparison at block 90.

After the comparison is performed, a comparator value may be assigned to each incoming signal at block 92. In certain embodiments, if the measured signal exceeds the threshold, the comparator value may equal one. If the measured signal is below the threshold, the comparator value may equal zero. At block 94, the comparator values from all four channels may be summed and the placement parameter may be determined from the sum at block 96.

Table I shows the possible sum totals of an embodiment of a tube 12 with four channels. In one embodiment, any combination in which the sum is less than or equal to one, the tube 12 may be determined to be a satisfactory distance from the carina 28. In Table I, such combinations are represented by examples 1-5.

TABLE I

| Example | Anterior Value | Posterior Value | Left Value | Right Value | SUM |
|---|---|---|---|---|---|
| 1 | 0 | 0 | 0 | 0 | 0 |
| 2 | 1 | 0 | 0 | 0 | 1 |
| 3 | 0 | 1 | 0 | 0 | 1 |
| 4 | 0 | 0 | 1 | 0 | 1 |
| 5 | 0 | 0 | 0 | 1 | 1 |
| 6 | 1 | 0 | 0 | 1 | 2 |
| 7 | 1 | 1 | 0 | 0 | 2 |
| 8 | 1 | 0 | 1 | 0 | 2 |
| 9 | 0 | 1 | 1 | 0 | 2 |
| 10 | 0 | 1 | 0 | 1 | 2 |
| 11 | 0 | 0 | 1 | 1 | 2 |
| 12 | 1 | 1 | 0 | 1 | 3 |
| 13 | 1 | 0 | 1 | 1 | 3 |
| 14 | 0 | 1 | 1 | 1 | 3 |
| 15 | 1 | 1 | 1 | 0 | 3 |
| 16 | 1 | 1 | 1 | 1 | 4 |

Similar tables may be developed for particular tube 12 arrangements with different numbers of and/or distributions of energy conducting channels 18. For example, for tubes with six channels, a sum of two or three may be associated with proper placement. In addition, for certain arrangements, certain sums of comparator values may serve as a reliable indicator of improper placement of the tube 12 too far away from a carina 28, while other sums may serve as a reliable indicator of improper placement of the tube 12 too close to a carina 28. In such embodiments, proper placement may involve a range of sums. Accordingly, rather than relying on a particular sum, other techniques for determining proper placement of the tube 12 may involve accessing a look-up table or direct comparison to a threshold.

When it is determined that the tube 12 is properly placed, a placement parameter may be output by the monitor 30 and may include a graphical, visual, or audio representation of the tube/anatomical structure distance. For example, a placement parameter associated with proper placement may include green light indicated on a display or a short tone generated by a speaker associated with monitor 30. Similarly, a placement parameter associated with improper placement of the tube 12 may trigger an alarm, which may include one or more of an audio or visual alarm indication. In one embodiment, the alarm may be triggered if the measured signal from multiple locations is greater than a predetermined threshold or greater than a predetermined sum of comparator values, or outside of a predetermined range of sums.

Figure 6:
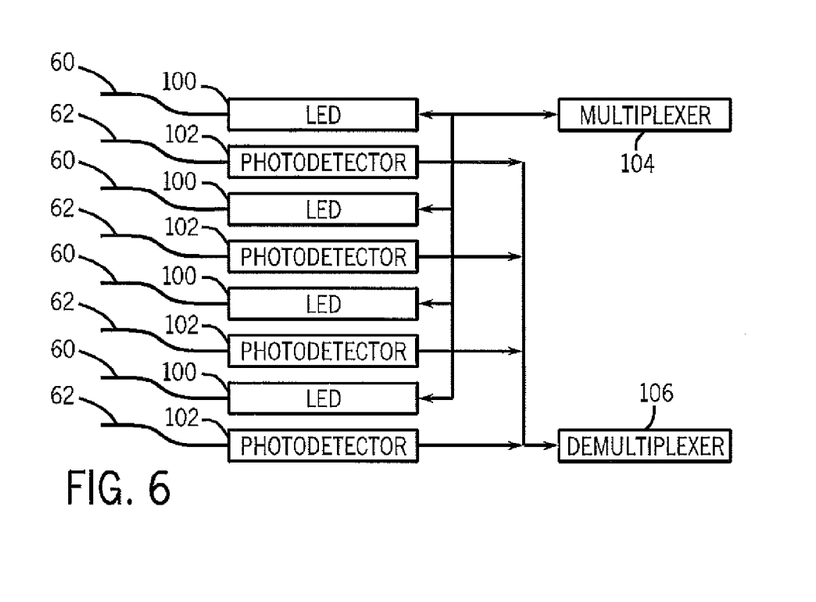
FIG. 6 is a block diagram of an exemplary arrangement of multiple optical channels of the tracheal tube.

As noted, tubes 12 as provided herein may employ multiple energy emitters, such as energy conducting channels 18 or energy emitters directly associated with the tube 12, to provide a rotation-independent determination of tube placement relative to a patient's airway anatomy. However, the use of multiple energy emitters may result in more complex signal processing relative to systems in which only one emitter is employed. FIG. 6 is an embodiment in which multiple LEDs 100 are employed as energy sources 24 and multiple photodetectors 102 are employed as detectors 26. The LEDs 100 may shine light through associated fibers 60 and the returned light may be transmitted to the detectors 102 through associated return fibers 62. The LEDs 100 may be multiplexed with a multiplexer 104, for example in the frequency domain or the time domain. In one embodiment, each individual LED 100 may be amplitude modulated at a different frequency and each individual photodetector 102 may be tuned to detect only the frequency corresponding to its associated LED 100. After the returned energy is detected, the photodetectors 102 may communicate a multiplexed signal that may be separated at demultiplexer 106.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube placement relative to anatomical structures in the trachea, but these techniques may also be utilized for the measurement and/or analysis of the placement of other suitable medical devices relative to other anatomical structures. For example, the present techniques may be utilized for the measurement and/or analysis of tracheal tubes relative to tracheal walls or the vocal cords. In addition, the present techniques may be employed in determining appropriate placement of any medical device, such as a stent, catheter, implant, feeding tube, cardiac device, drug delivery device, or pump. Rather, the various embodiments may cover all modifications, equivalents, and alternatives falling within the spirit and scope of the disclosure as defined by the following appended claims.

What is claimed is:

1. A system for determining placement of a tracheal tube in a subject comprising:
    a tracheal tube comprising a plurality of optical conductors disposed circumferentially about a wall of the tracheal tube, wherein the plurality of optical conductors comprises at least four optical conductors having distal ends terminating at locations spaced about a circumference of the tracheal tube such that respective distal ends of the plurality of optical conductors correspond to an anterior, posterior, right, and left location of the tracheal tube;
    one or more light sources configured to emit light through each of the respective plurality of optical conductors when the tracheal tube is disposed in a subject;
    one or more light detectors configured to receive returned light from each of the respective plurality of optical conductors;
    a processor configured to determine a placement parameter based upon the returned light, wherein determining the placement parameter comprises:
    comparing the returned light from each respective location to a threshold to generate respective comparator values associated with each of the anterior, posterior, right, and left locations; and
    determining that the tracheal tube is properly placed based at least in part on a sum of the respective comparator values.

2. The system of claim 1, wherein the plurality of optical conductors are disposed within a wall of the tube.

3. The system of claim 1, wherein one or more of the plurality of optical conductors are configured to transmit light from a region proximate a distal end of the tube.

4. The system of claim 1, wherein at least some of the plurality of optical conductors are evenly spaced about a circumference of the wall.

5. The system of claim 1, wherein the optical conductors comprise optical fibers.

6. The system of claim 1, comprising an alarm configured to be triggered when the placement parameter indicates that the tracheal tube is not properly placed.

7. The system of claim 1, wherein the threshold comprises an empirically derived optical intensity threshold.

8. The system of claim 1, wherein determining the placement parameter comprises determining whether the sum of the respective comparator values is less than or equal to a desired integer value.

9. The system of claim 1, wherein the processor determines that the tracheal tube is properly placed when none of the anterior, posterior, left, or right comparator values exceeds the threshold.

10. The system of claim 1 wherein the processor determines that the tracheal tube is properly placed when one of the anterior, posterior, left, or right comparator values exceeds the threshold.

11. The system of claim 1, wherein the processor determines that the tracheal tube is improperly placed when two or more of the anterior, posterior, left, or right comparator values exceeds the threshold.

12. The system of claim 1, wherein determining that the tracheal tube is properly placed comprises comparing the sum of the respective comparator values to a range of sums.

13. A system for determining placement of a tracheal tube in a subject comprising:
a monitor comprising a processor configured to:
receive a first signal from a first location on a tracheal tube;
receive a second signal from a second location on the tracheal tube;
compare the first signal to a threshold to generate a first comparator value;
compare the second signal to the threshold to generate a second comparator value; and
determine a placement parameter of the tracheal tube based at least in part on a sum of the first comparator value and the second comparator value.

14. The system of claim 13, wherein the processor is configured to:
receive a third signal and a fourth signal from more additional locations on the tracheal tube;
compare the third signal and the fourth signal to the threshold to generate a third comparator value and a fourth comparator value; and
determine the placement parameter based at least in part on the sum of the first comparator value and the second comparator value and a second sum of the third comparator value and the fourth comparator value.

15. The system of claim 13, wherein the first signal and the second signal represent optical information.

16. The system of claim 15, wherein the threshold comprises an empirically derived optical intensity threshold.

17. The system of claim 13, wherein the first signal and the second signal represent ultrasound information.

18. The system of claim 17, wherein the threshold comprises an empirically derived ultrasound intensity threshold.

19. The system of claim 13, wherein the first comparator value and the second comparator value are either one or zero, and wherein determining the placement parameter comprises determining whether the sum of the first comparator value and the second comparator value is less than or equal to a desired integer value.

20. A method for determining placement of a tracheal tube in a subject comprising:
receiving a first signal from a first location on a tracheal tube;
receiving a second signal from a second location on the tracheal tube;
comparing the first signal to a threshold to generate a first comparator value;
comparing the second signal to the threshold to generate a second comparator value; and
determining a placement parameter of the tracheal tube based at least in part on a sum of the first comparator value and the second comparator value.

21. The method of claim 20, wherein comparing the first signal or the second signal to a threshold to generate a first comparator value or a second comparator value comprises determining a time of flight of returned energy.

22. The method of claim 20, wherein comparing the first signal or the second signal to a threshold to generate a first comparator value or a second comparator value comprises determining an intensity of the returned energy.

23. The method of claim 20, wherein the steps are performed after intubation of the subject.

24. The method of claim 20, wherein determining the placement parameter comprises determining whether the sum is less than or equal to a desired integer value.

* * * * *